US00PP16250P2

(12) United States Plant Patent
Zary

(10) Patent No.: US PP16,250 P2
(45) Date of Patent: Feb. 14, 2006

(54) FLORIBUNDA ROSE PLANT NAMED 'JACARQUE'

(50) Latin Name: *Rosa hybrida*
Varietal Denomination: JACarque

(75) Inventor: Keith W. Zary, Somis, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 34 days.

(21) Appl. No.: 10/848,733

(22) Filed: May 18, 2004

(51) Int. Cl.
*A01H 5/00* (2006.01)

(52) U.S. Cl. ..... Plt./145

(58) Field of Classification Search ..... Plt./145, Plt./146, 141, 104
See application file for complete search history.

(56) References Cited

PUBLICATIONS

UPOV–ROM GTITM, Plant Variety Database, 2004/04, GTI Jouve Retrieval Software, Citation for Rosa 'Jacarque'.*

* cited by examiner

*Primary Examiner*—Anne Marie Grunberg
*Assistant Examiner*—June Hwu
(74) *Attorney, Agent, or Firm*—Klarquist Sparkman LLP

(57) ABSTRACT

Floribunda rose plant having an apricot gold flower color; resistance to blackspot and rust; strong, sweet fragrance; blooming in clusters; and upright, compact plant habit.

1 Drawing Sheet

Genus and species: *Rosa hybrida*.
Variety denomination: 'JACarque'.

ORIGIN OF THE INVENTION

The present invention relates to a new and distinct variety of floribunda rose plant named 'JACarque' which was originated by me by crossing the variety 'AROfres,' (not patented), with the variety 'HARroony'(Amber Queen), U.S. Plant Pat. No. 5,582.

BACKGROUND OF THE INVENTION

The primary objective of this breeding was to produce a new rose variety having healthy, disease-resistant foliage; upright, rounded, compact plant habit; golden apricot flower color; and strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Beautiful apricot gold flower color.
2. Resistant to blackspot and rust.
3. Strong, sweet fragrance.
4. Blooms in clusters.
5. Upright, compact plant habit.

Asexual reproduction of this new variety by budding, as performed at Wasco and Somis, Calif., shows that the foregoing and all other characteristics and distinctions come true to form and are established and transmitted through succeeding propagations.

COMPARISON WITH PARENTS

The subject variety differs from 'AROfres' in flower color in that 'AROfres' is light yellow over the entire petal surface while 'JACarque' is Yellow-Orange. 'JACarque' also differs from 'AROfres' in fragrance in that 'AROfres' is not fragrant. 'JACarque' differs from 'HARroony' in that 'HARroony' has no orange tones at all and 'JACarque' is also much less spreading than 'HARroony'.

COMPARISON WITH SIMILAR VARIETY

The variety most similar to 'JACarque' is 'HARroony' which differs from 'JACarque' as noted above.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'AROfres'.
*Pollen parent.*—'HARroony' (Amber Queen). U.S. Plant Pat. No. 5,582.

FLOWER

Observations made from plants commencing at two years of age grown in a garden environment at Somis and Wasco, Calif.

Blooming habit: Continuous.

Bud:

*Size.*—About 3.5–4 cm long and 2–2.5 cm in diameter when the petals start to unfurl.

*Form.*—The bud form is long, pointed ovoid.

*Color.*—When sepals first divide, bud color is Yellow-Orange Group 16C often with outer petals Orange-Red Group N 30C. Guard petals occasionally have Yellow-Green Group 145B streak. When half blown, the upper sides of the petals are Yellow-Orange Group 16B; and the lower sides of the petals are Yellow-Orange Group 16C.

*Sepals.*—Color: Upper surface: Yellow-Green Group 144B with prominent Yellow-Green Group 144D stripe running lengthwise in the center. Lower surface: Yellow-Green Group 144A with Yellow-Green Group N 144D at the sepal base. Length: 31–34 mm. Width: 9–11 mm. Shape: Subulate. Surface texture: Upper surface: Canescent. Lower surface: Hoary. There are three lightly appendaged sepals. There are two unappendaged sepals with glandular edges.

*Receptacle.*—Color: Yellow-Green Group 144A. Shape: Funnel. Size: Medium, about 6–8 mm long× 9–10 mm wide. Surface: Smooth, with very tiny white hairs.

*Peduncle.*—Length: Medium, averaging about 6–12 cm. Surface: Prickly, glandular. Color: Yellow-Green Group 144A. Strength: Stiff.

Bloom:

*Size.*—Medium. Average open diameter is about 10–12 cm.

*Borne.*—In pyramidal clusters of 5–7.

*Stems.*—Strength: Strong. Average length is about 30–40 cm with a diameter of 5–6 cm. Color: Green Group 143C.

*Form.*—When first open: Cupped, full of petals. Permanence: Outer petal edges curl slightly.

*Petalage.*—Number of petals under normal conditions: 30–35. Color: The upper sides of the petals are Yellow-Orange Group 16B. The reverse sides of the petals are Yellow-Orange Group 16C. The base of each petal is Yellow Group 13A. The major color on the upper side is Yellow-Orange Group 16B.

*Variegations.*—None.

*Discoloration.*—The general tonality at the end of the first day: Yellow-Orange Group 16B. At the end of the third day: Yellow-Orange Group 16B. Further aging: Day five fades to Yellow-Orange Group 18C.

*Fragrance.*—Strong, sweet, honey.

Petals:

*Texture.*—Thick.

*Shape.*—Obovate.

*Surface.*—Smooth.

*Margin.*—Entire. Apex Shape: Cuspidate. Base Shape: Cuneate.

*Form.*—Tips slightly recurved.

*Arrangement.*—Imbricated.

*Petaloids.*—Number: 3–5 Color: Yellow-Orange Group 16B. Length: 3–7 mm. Width: 1–3 mm.

*Persistence.*—Petals drop off cleanly before drying.

*Lastingness.*—On the plant: Long (about 5–7 days). As a cut flower: Long (about 7–9 days).

Reproductive parts:

*Stamens.*—Number: 130–150. Length: 12–14 mm. Anthers: Length: 2–3 mm. Color: Yellow-Orange Group 21B. Arrangement: Regular around styles. Filaments: Color: Yellow Group 13B. Length: 10–12 mm. Pollen: Color: None observed.

*Pistils.*—Number: 110–130. Length: 7–10 mm. Styles: Color: Bottom ½: Yellow Group 2D, Top ½: Red Group 50A. Length: 6–9 mm. Stigmas: Color: Yellow-Orange Group 22B. Length: 1 mm.

*Hips.*—None observed.

PLANT

*Form.*—Bush.

*Growth.*—Vigorous, upright, branching, compact.

*Age at maturity.*—2 years.

*Mature plant.*—Height: 110 cm. Width: 90 cm.

*Rootstock.*—Dr. Huey.

Foliage: Number of leaflets on normal mid-stem leaves: 7.

*Size.*—Large. About 16–20 cm long×12–14 cm wide.

*Quantity.*—Normal.

*Color.*—New foliage: Upper side: Greyed-Red Group 178A. Lower side: Greyed-Purple Group 184B. Old foliage: Upper side: Yellow-Green Group 147A. Lower side: Yellow-Green Group 147C.

Leaflets:

*Size.*—About 6–8 cm long×4–5 cm wide.

*Shape.*—Broadly oval.

*Base shape.*—Rounded.

*Apex shape.*—Acuminate.

*Texture.*—Coriaceous.

*Edge.*—Serrated.

*Serrations.*—Single.

*Petiole.*—Color: Greyed-Yellow Group 160C. Average Length: 12–13 mm. Surface Texture: Smooth.

*Petiole rachis.*—Color: Upper side: Yellow-Green Group 146D. Upper side: Greyed-Yellow Group 160C; with prickles and glands.

*Auricle.*—None.

*Stipules.*—Length: 22–25 mm, edges glandular. Color: Upper side: Yellow-Green Group 147A. Lower side: Yellow-Green Group 147C.

*Disease resistance.*—Resistant to blackspot and rust and susceptible to mildew under normal growing conditions.

*Pest resistance.*—Not observed.

*Vein color.*—Yellow-Green Group 147D.

*Venation pattern.*—Reticulate.

Wood:

*New wood.*—Color: Red Group 47A. Bark: Smooth, glandular.

*Old wood.*—Color: Green Group 143C. Bark: Smooth.

Prickles:

*Quantity.*—On main canes from base: Few. On laterals from main canes: Ordinary (5–7 per 20 cm of stem).

*Form.*—Straight.

*Length.*—9–11 mm.

*Color when young.*—Greyed-Red Group 181B.

*Color when mature.*—Greyed-Yellow Group 160C.

Small prickles:

*Quantity.*—On main stalks: None. On laterals: Few.

*Color.*—Greyed-Red Group 181B.

Winter hardiness: Hardy to Zone 5.

I claim:

1. A new and distinct variety of rose plant of the floribunda class, substantially as herein shown and described, characterized particularly by its apricot gold flower color; resistance to blackspot and rust; strong, sweet fragrance; blooming in clusters; and upright, compact plant habit.

* * * * *

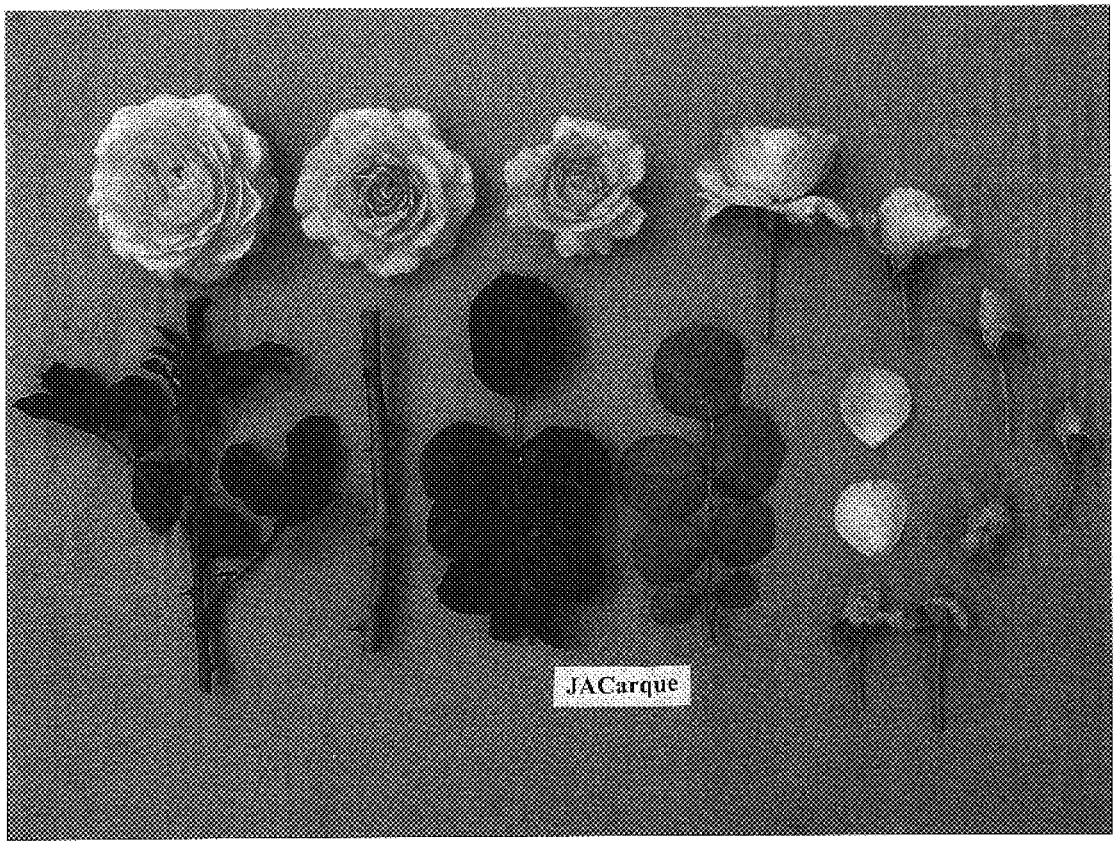
JACarque